US009014387B2

(12) United States Patent
Hendrix et al.

(10) Patent No.: US 9,014,387 B2
(45) Date of Patent: Apr. 21, 2015

(54) COORDINATED CONTROL OF ADAPTIVE NOISE CANCELLATION (ANC) AMONG EARSPEAKER CHANNELS

(71) Applicant: Cirrus Logic, Inc., Austin, TX (US)

(72) Inventors: Jon D. Hendrix, Wimberly, TX (US); Jeffrey Alderson, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 233 days.

(21) Appl. No.: 13/795,160

(22) Filed: Mar. 12, 2013

(65) Prior Publication Data

US 2013/0287219 A1 Oct. 31, 2013

Related U.S. Application Data

(60) Provisional application No. 61/638,607, filed on Apr. 26, 2012.

(51) Int. Cl.
*A61F 11/06* (2006.01)
*G10K 11/16* (2006.01)
(Continued)

(52) U.S. Cl.
CPC .......... *G10K 11/175* (2013.01); *G10K 11/1786* (2013.01); *G10K 2210/1081* (2013.01); *G10K 2210/30391* (2013.01); *G10K 2210/3055* (2013.01); *G10K 2210/503* (2013.01)

(58) Field of Classification Search
CPC ............. H04R 1/1083; G10K 11/1786; G10K 2210/1081; G10K 2210/108; G10K 11/178
USPC ................ 381/71.1, 71.2, 71.6, 71.11, 71.12, 381/71.8, 94.1, 58, 74, 122
See application file for complete search history.

(56) References Cited

U.S. PATENT DOCUMENTS

| | | | |
|---|---|---|---|
| 5,251,263 | A | 10/1993 | Andrea et al. |
| 5,278,913 | A | 1/1994 | Delfosse et al. |

(Continued)

FOREIGN PATENT DOCUMENTS

| | | | |
|---|---|---|---|
| DE | 102011013343 | A1 | 9/2012 |
| EP | 1880699 | A2 | 1/2008 |

(Continued)

OTHER PUBLICATIONS

Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.

(Continued)

*Primary Examiner* — Xu Mei
*Assistant Examiner* — Douglas Suthers
(74) *Attorney, Agent, or Firm* — Mitch Harris, Atty at Law, LLC; Andrew M. Harris

(57) ABSTRACT

A personal audio device including earspeakers, includes an adaptive noise canceling (ANC) circuit that adaptively generates an anti-noise signal for each earspeaker from at least one microphone signal that measures the ambient audio, and the anti-noise signals are combined with source audio to provide outputs for the earspeakers. The anti-noise signals cause cancellation of ambient audio sounds at the respective earspeakers. A processing circuit uses the microphone signal(s) to generate the anti-noise signals, which can be generated by adaptive filters. The processing circuit controls adaptation of the adaptive filters such that when an event requiring action on the adaptation of one of the adaptive filters is detected, action is taken on the other one of the adaptive filters. Another feature of the ANC system uses microphone signals provided at both of the earspeakers to perform processing on a voice microphone signal that receives speech of the user.

24 Claims, 5 Drawing Sheets

(51) Int. Cl.

| | |
|---|---|
| ***H03B 29/00*** | (2006.01) |
| ***H04R 1/10*** | (2006.01) |
| ***H04R 29/00*** | (2006.01) |
| ***G10K 11/175*** | (2006.01) |
| ***G10K 11/178*** | (2006.01) |

(56) References Cited

U.S. PATENT DOCUMENTS

| | | | |
|---|---|---|---|
| 5,337,365 | A | 8/1994 | Hamabe et al. |
| 5,410,605 | A | 4/1995 | Sawada et al. |
| 5,425,105 | A | 6/1995 | Lo et al. |
| 5,586,190 | A | 12/1996 | Trantow et al. |
| 5,640,450 | A | 6/1997 | Watanabe |
| 5,699,437 | A | 12/1997 | Finn |
| 5,706,344 | A | 1/1998 | Finn |
| 5,768,124 | A | 6/1998 | Stothers et al. |
| 5,815,582 | A | 9/1998 | Claybaugh et al. |
| 5,946,391 | A | 8/1999 | Dragwidge et al. |
| 5,991,418 | A | 11/1999 | Kuo |
| 6,041,126 | A | 3/2000 | Terai et al. |
| 6,118,878 | A | 9/2000 | Jones |
| 6,219,427 | B1 | 4/2001 | Kates et al. |
| 6,418,228 | B1 | 7/2002 | Terai et al. |
| 6,434,246 | B1 | 8/2002 | Kates et al. |
| 6,434,247 | B1 | 8/2002 | Kates et al. |
| 6,768,795 | B2 | 7/2004 | Feltstrom et al. |
| 6,850,617 | B1 | 2/2005 | Weigand |
| 7,058,463 | B1 | 6/2006 | Ruha et al. |
| 7,103,188 | B1 | 9/2006 | Jones |
| 7,181,030 | B2 | 2/2007 | Rasmussen et al. |
| 7,330,739 | B2 | 2/2008 | Somayajula |
| 7,365,669 | B1 | 4/2008 | Melanson |
| 7,742,790 | B2 | 6/2010 | Konchitsky et al. |
| 8,019,050 | B2 | 9/2011 | Mactavish et al. |
| 8,249,262 | B2 | 8/2012 | Chua et al. |
| 8,290,537 | B2 | 10/2012 | Lee et al. |
| 8,379,884 | B2 | 2/2013 | Horibe et al. |
| 8,401,200 | B2 | 3/2013 | Tiscareno et al. |
| 2001/0053228 | A1 | 12/2001 | Jones |
| 2002/0003887 | A1 | 1/2002 | Zhang et al. |
| 2004/0165736 | A1 | 8/2004 | Hetherington et al. |
| 2004/0167777 | A1 | 8/2004 | Hetherington et al. |
| 2004/0264706 | A1 | 12/2004 | Ray et al. |
| 2005/0117754 | A1 | 6/2005 | Sakawaki |
| 2005/0240401 | A1 | 10/2005 | Ebenezer |
| 2006/0153400 | A1 | 7/2006 | Fujita et al. |
| 2007/0030989 | A1 | 2/2007 | Kates |
| 2007/0033029 | A1 | 2/2007 | Sakawaki |
| 2007/0038441 | A1 | 2/2007 | Inoue et al. |
| 2007/0053524 | A1 | 3/2007 | Haulick et al. |
| 2007/0076896 | A1 | 4/2007 | Hosaka et al. |
| 2007/0154031 | A1 | 7/2007 | Avendano et al. |
| 2007/0258597 | A1 | 11/2007 | Rasmussen et al. |
| 2007/0297620 | A1 | 12/2007 | Choy |
| 2008/0019548 | A1 | 1/2008 | Avendano |
| 2008/0181422 | A1 | 7/2008 | Christoph |
| 2008/0226098 | A1 | 9/2008 | Haulick et al. |
| 2009/0012783 | A1 | 1/2009 | Klein |
| 2009/0034748 | A1 | 2/2009 | Sibbald |
| 2009/0041260 | A1 | 2/2009 | Jorgensen et al. |
| 2009/0046867 | A1 | 2/2009 | Clemow |
| 2009/0196429 | A1 | 8/2009 | Ramakrishnan et al. |
| 2009/0220107 | A1 | 9/2009 | Every et al. |
| 2009/0238369 | A1 | 9/2009 | Ramakrishnan et al. |
| 2009/0245529 | A1 | 10/2009 | Asada et al. |
| 2009/0254340 | A1 | 10/2009 | Sun et al. |
| 2009/0290718 | A1 | 11/2009 | Kahn et al. |
| 2009/0296965 | A1 | 12/2009 | Kojima |
| 2009/0304200 | A1 | 12/2009 | Kim et al. |
| 2010/0014683 | A1 | 1/2010 | Maeda et al. |
| 2010/0014685 | A1 | 1/2010 | Wurm |
| 2010/0061564 | A1 | 3/2010 | Clemow et al. |
| 2010/0069114 | A1 | 3/2010 | Lee et al. |
| 2010/0082339 | A1 | 4/2010 | Konchitsky et al. |
| 2010/0098263 | A1 | 4/2010 | Pan et al. |
| 2010/0124336 | A1 | 5/2010 | Shridhar et al. |
| 2010/0166203 | A1 | 7/2010 | Peissig et al. |
| 2010/0195838 | A1 | 8/2010 | Bright |
| 2010/0195844 | A1 | 8/2010 | Christoph et al. |
| 2010/0272276 | A1 | 10/2010 | Carreras et al. |
| 2010/0272283 | A1 | 10/2010 | Carreras et al. |
| 2010/0274564 | A1 | 10/2010 | Bakalos et al. |
| 2010/0296666 | A1 | 11/2010 | Lin |
| 2010/0296668 | A1 | 11/2010 | Lee et al. |
| 2010/0310086 | A1 | 12/2010 | Magrath et al. |
| 2010/0322430 | A1 | 12/2010 | Isberg |
| 2011/0007907 | A1 | 1/2011 | Park et al. |
| 2011/0106533 | A1 | 5/2011 | Yu |
| 2011/0142247 | A1 | 6/2011 | Fellers et al. |
| 2011/0144984 | A1 | 6/2011 | Konchitsky |
| 2011/0158419 | A1 | 6/2011 | Theverapperuma et al. |
| 2011/0222698 | A1 | 9/2011 | Asao et al. |
| 2011/0249826 | A1 | 10/2011 | Van Leest |
| 2011/0288860 | A1 | 11/2011 | Schevciw et al. |
| 2011/0293103 | A1 | 12/2011 | Park et al. |
| 2011/0299695 | A1 | 12/2011 | Nicholson |
| 2011/0317848 | A1 | 12/2011 | Ivanov et al. |
| 2012/0135787 | A1 | 5/2012 | Kusunoki et al. |
| 2012/0140943 | A1 | 6/2012 | Hendrix et al. |
| 2012/0170766 | A1 | 7/2012 | Alves et al. |
| 2012/0207317 | A1 | 8/2012 | Abdollahzadeh Milani et al. |
| 2012/0250873 | A1 | 10/2012 | Bakalos et al. |
| 2012/0259626 | A1 | 10/2012 | Li et al. |
| 2012/0300958 | A1 | 11/2012 | Klemmensen |
| 2012/0308021 | A1 | 12/2012 | Kwatra et al. |
| 2012/0308024 | A1 | 12/2012 | Alderson et al. |
| 2012/0308025 | A1 | 12/2012 | Hendrix et al. |
| 2012/0308026 | A1 | 12/2012 | Kamath et al. |
| 2012/0308027 | A1 | 12/2012 | Kwatra |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0086425 | A1 | 3/2014 | Jensen et al. |
| 2014/0177851 | A1 | 6/2014 | Kitazawa et al. |
| 2014/0211953 | A1 | 7/2014 | Alderson et al. |
| 2014/0270222 | A1 | 9/2014 | Hendrix et al. |
| 2014/0270223 | A1 | 9/2014 | Li et al. |
| 2014/0270224 | A1 | 9/2014 | Zhou et al. |

FOREIGN PATENT DOCUMENTS

| | | | |
|---|---|---|---|
| EP | 1947642 | A1 | 7/2008 |
| EP | 2133866 | A1 | 12/2009 |
| EP | 2216774 | A1 | 8/2010 |
| EP | 2395500 | A1 | 12/2011 |
| EP | 2395501 | A1 | 12/2011 |
| GB | 2401744 | A | 11/2004 |
| GB | 2455821 | A | 6/2009 |
| GB | 2455824 | A | 6/2009 |
| GB | 2455828 | A | 6/2009 |
| GB | 2484722 | A | 4/2012 |
| JP | H06-186985 | A | 7/1994 |
| WO | WO 03/015074 | A1 | 2/2003 |
| WO | WO 2004009007 | A1 | 1/2004 |
| WO | WO 2007007916 | A1 | 1/2007 |
| WO | WO 2007113487 | A1 | 11/2007 |
| WO | WO 2010117714 | A1 | 10/2010 |
| WO | WO 2012134874 | A1 | 10/2012 |

OTHER PUBLICATIONS

Jin, et al. "A simultaneous equation method-based online secondary path modeling algorithm for active noise control", Journal of Sound

(56) References Cited

OTHER PUBLICATIONS and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.
Parkins, et al., "Narrowband and broadband active control in an enclosure using the acoustic energy density", J. Acoust. Soc. Am. Jul. 2000, pp. 192-203, vol. 108, issue 1, US.
Feng, et al.., "A broadband self-tuning active noise equaliser", Signal Processing, Oct. 1, 1997, pp. 251-256, vol. 62, No. 2, Elsevier Science Publishers B.V. Amsterdam, NL.
Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
International Search Report and Written Opinion in PCT/US2013/034808, mailed on Mar. 21, 2014, 18 pages (pp. 1-18 in pdf).
International Preliminary Report on Patentability in PCT/US2013/034808, mailed on Sep. 10, 2014, 20 pages (pp. 1-20 in pdf).
U.S. Appl. No. 13/686,353, filed Nov. 27, 2012, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
U.S. Appl. No. 14/029,159, filed Sep. 17, 2013, Li, et al.
U.S. Appl. No. 14/062,951, filed Oct. 25, 2013, Zhou, et al.
U.S. Appl. No. 14/197,814, filed Mar. 5, 2014, Kaller, et al.

(56) References Cited

OTHER PUBLICATIONS

U.S. Appl. No. 14/210,537, filed Mar. 14, 2014, Abdollahzadeh Milani, et al.

U.S. Appl. No. 14/210,589, filed Mar. 14, 2014, Abdollahzadeh Milani, et al.

Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.

Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.

Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.

Liu, et al., "Compensatory Responses to Loudness-shifted Voice Feedback During Production of Mandarin Speech", Journal of the Acoustical Society of America, Oct. 2007, pp. 2405-2412, vol. 122, No. 4.

Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.

Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.

COORDINATED CONTROL OF ADAPTIVE NOISE CANCELLATION (ANC) AMONG EARSPEAKER CHANNELS

This U.S. Patent Application claims priority under 35 U.S.C. 119(e) to U.S. Provisional Patent Application Ser. No. 61/638,607 filed on Apr. 26, 2012.

BACKGROUND OF THE INVENTION

1. Field of the Invention

The present invention relates generally to personal audio devices, such as headphones, that include adaptive noise cancellation (ANC), and, more specifically, to architectural features of an ANC system in which control of an ANC system serving separate earspeakers is coordinated between channels.

2. Background of the Invention

Wireless telephones, such as mobile/cellular telephones, cordless telephones, and other consumer audio devices, such as MP3 players, are in widespread use. Performance of such devices with respect to intelligibility can be improved by providing noise canceling using a reference microphone to measure ambient acoustic events and then using signal processing to insert an anti-noise signal into the output of the device to cancel the ambient acoustic events.

Since the acoustic environment around personal audio devices, such as wireless telephones and earspeakers, can change dramatically, depending on the sources of noise that are present and the position of the devices themselves, it is desirable to adapt the noise canceling to take into account such environmental changes.

Therefore, it would be desirable to provide a personal audio system including earspeakers that provides noise cancellation in a variable acoustic environment.

SUMMARY OF THE INVENTION

The above-stated objective of providing a personal audio system including earspeakers that provides noise cancellation in a variable acoustic environment, is accomplished in a personal audio system, a method of operation, and an integrated circuit.

The personal audio system includes a pair of earspeakers, each having an output transducer for reproducing an audio signal that includes both source audio for playback to a listener and a corresponding anti-noise signal for countering the effects of ambient audio sounds in an acoustic output of the corresponding transducer. The personal audio device also includes the integrated circuit to provide adaptive noise-canceling (ANC) functionality. The method is a method of operation of the personal audio system and integrated circuit. At least one microphone provides at least one microphone signal indicative of the ambient audio sounds. The personal audio system further includes an ANC processing circuit for adaptively generating an anti-noise signal from the at least one microphone signal, such that the anti-noise signals cause substantial cancellation of the ambient audio sounds at the corresponding transducers. The ANC processing circuit further detects when action should be taken on adaptation of one of the adaptive filters and, in response, takes further action on adaptation of the other adaptive filter.

In another feature, the personal audio system includes two microphones, one for each earspeaker. The personal audio system measures the ambient audio at the earspeakers using a corresponding one of the two microphones, and generates a corresponding anti-noise signal that is supplied to the corresponding transducer of the earspeakers. The personal audio system further measures near speech of a user of the personal audio system and performs further processing on the near speech in conformity with the outputs of each of the two microphones.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

Noise-canceling techniques and circuits are disclosed that can be implemented in a personal audio device, such as a wireless telephone. The personal audio device includes a pair of earspeakers, each with a corresponding adaptive noise canceling (ANC) channel that measures the ambient acoustic environment and generates a signal that is injected into the earspeaker transducer to cancel ambient acoustic events. A microphone, which may be a pair of microphones—one on each earspeaker, is provided to measure the ambient acoustic environment, which is provided to adaptive filters of the ANC channels to generate anti-noise signals provided to the transducers to cancel the ambient audio sounds. Control of the ANC channels is performed, such that when an event is detected that requires action on adaptation of the adaptive filter for a first channel, action is also taken on the other channel. In another feature of the disclosed devices, near speech measured by a near speech microphone can be processed in accordance with ambient sound measurements made by a pair of microphones located on the earspeakers.

Figure 1A:
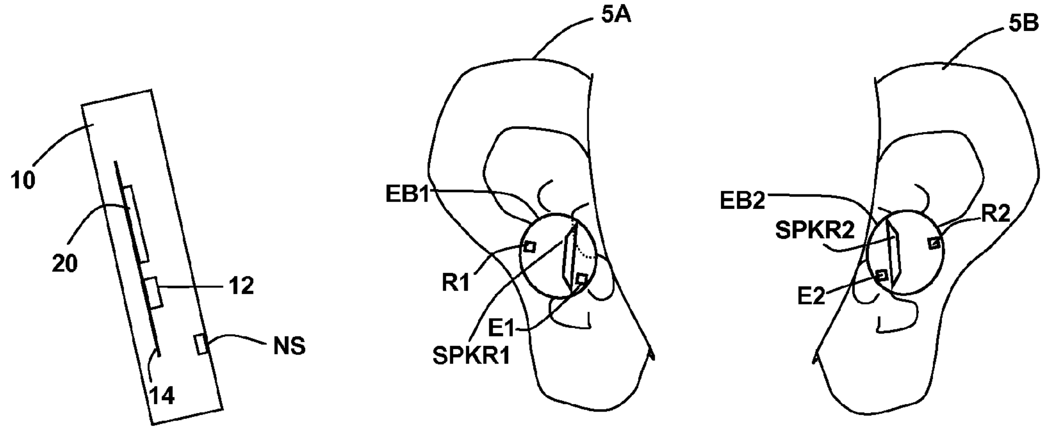
FIG. 1A is an illustration of a wireless telephone 10 coupled to a pair of earbuds EB1 and EB2, which is an example of a personal audio system in which the techniques disclosed herein can be implemented.

FIG. 1A shows a wireless telephone 10 and a pair of earbuds EB1 and EB2, each attached to a corresponding ear 5A, 5B of a listener. Illustrated wireless telephone 10 is an example of a device in which the techniques herein may be employed, but it is understood that not all of the elements or configurations illustrated in wireless telephone 10, or in the circuits depicted in subsequent illustrations, are required. Wireless telephone 10 is connected to earbuds EB1, EB2 by a wired or wireless connection, e.g., a BLUETOOTH™ connection (BLUETOOTH is a trademark of Bluetooth SIG, Inc.). Earbuds EB1, EB2 each have a corresponding transducer, such as speaker SPKR1, SPKR2, which reproduce source audio including distant speech received from wireless telephone 10, ringtones, stored audio program material, and injection of near-end speech (i.e., the speech of the user of wireless telephone 10). The source audio also includes any other audio that wireless telephone 10 is required to reproduce, such as source audio from web-pages or other network communications received by wireless telephone 10 and audio indications such as battery low and other system event notifications. Reference microphones R1, R2 are provided on a surface of the housing of respective earbuds EB1, EB2 for measuring the ambient acoustic environment. Another pair of microphones, error microphones E1, E2, are provided in order to further improve the ANC operation by providing a measure of the ambient audio combined with the audio reproduced by respective speakers SPKR1, SPKR2 close to corresponding ears 5A, 5B, when earbuds EB1, EB2 are inserted in the outer portion of ears 5A, 5B.

Wireless telephone 10 includes adaptive noise canceling (ANC) circuits and features that inject an anti-noise signal into speakers SPKR1, SPKR2 to improve intelligibility of the distant speech and other audio reproduced by speakers SPKR1, SPKR2. Exemplary circuit 14 within wireless telephone 10 includes an audio integrated circuit 20 that receives the signals from reference microphones R1, R2, near speech microphone NS, and error microphones E1, E2 and interfaces with other integrated circuits such as an RF integrated circuit 12 containing the wireless telephone transceiver. In other implementations, the circuits and techniques disclosed herein may be incorporated in a single integrated circuit that contains control circuits and other functionality for implementing the entirety of the personal audio device, such as an MP3 player-on-a-chip integrated circuit. Alternatively, the ANC circuits may be included within a housing of earbuds EB1, EB2 or in a module located along wired connections between wireless telephone 10 and earbuds EB1, EB2. For the purposes of illustration, the ANC circuits will be described as provided within wireless telephone 10, but the above variations are understandable by a person of ordinary skill in the art and the consequent signals that are required between earbuds EB1, EB2, wireless telephone 10, and a third module, if required, can be easily determined for those variations. A near speech microphone NS is provided at a housing of wireless telephone 10 to capture near-end speech, which is transmitted from wireless telephone 10 to the other conversation participant(s). Alternatively, near speech microphone NS may be provided on the outer surface of a housing of one of earbuds EB1, EB2, on a boom affixed to one of earbuds EB1, EB2, or on a pendant located between wireless telephone 10 and either or both of earbuds EB1, EB2.

Figure 1B:
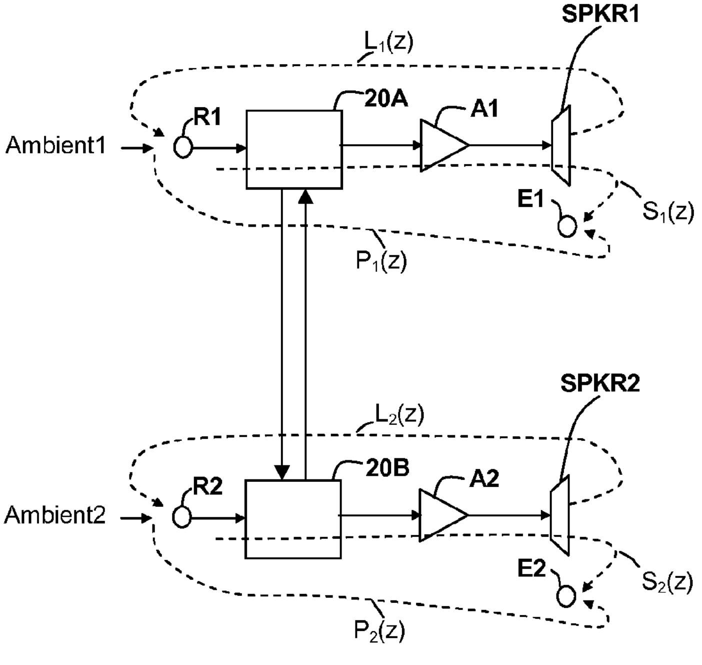
FIG. 1B is an illustration of electrical and acoustical signal paths in FIG. 1A.

FIG. 1B shows a simplified schematic diagram of audio integrated circuits 20A, 20B that include ANC processing, as coupled to reference microphones R1, R2, which provides a measurement of ambient audio sounds Ambient1, Ambient 2 that is filtered by the ANC processing circuits within audio integrated circuits 20A, 20B, located within corresponding earbuds EB1, EB2. Audio integrated circuits 20A, 20B may be alternatively combined in a single integrated circuit such as integrated circuit 20 within wireless telephone 10. Audio integrated circuits 20A, 20B generate outputs for their corresponding channels that are amplified by an associated one of amplifiers A1, A2 and which are provided to the corresponding one of speakers SPKR1, SPKR2. Audio integrated circuits 20A, 20B receive the signals (wired or wireless depending on the particular configuration) from reference microphones R1, R2, near speech microphone NS and error microphones E1, E2. Audio integrated circuits 20A, 20B also interface with other integrated circuits such as an RF integrated circuit 12 containing the wireless telephone transceiver shown in FIG. 1A. In other configurations, the circuits and techniques disclosed herein may be incorporated in a single integrated circuit that contains control circuits and other functionality for implementing the entirety of the personal audio device, such as an MP3 player-on-a-chip integrated circuit. Alternatively, multiple integrated circuits may be used, for example, when a wireless connection is provided from each of earbuds EB1, EB2 to wireless telephone 10 and/or when some or all of the ANC processing is performed within earbuds EB1, EB2 or a module disposed along a cable connecting wireless telephone 10 to earbuds EB1, EB2.

In general, the ANC techniques illustrated herein measure ambient acoustic events (as opposed to the output of speakers SPKR1, SPKR2 and/or the near-end speech) impinging on reference microphones R1, R2 and also measure the same ambient acoustic events impinging on error microphones E1, E2. The ANC processing circuits of integrated circuits 20A, 20B individually adapt an anti-noise signal generated from the output of the corresponding reference microphone R1, R2 to have a characteristic that minimizes the amplitude of the ambient acoustic events at the corresponding error microphone E1, E2. Since acoustic path $P_1(z)$ extends from reference microphone R1 to error microphone E1, the ANC circuit in audio integrated circuit 20A is essentially estimating acoustic path $P_1(z)$ combined with removing effects of an electro-acoustic path $S_1(z)$ that represents the response of the audio output circuits of audio integrated circuit 20A and the acoustic/electric transfer function of speaker SPKR1. The estimated response includes the coupling between speaker SPKR1 and error microphone E1 in the particular acoustic environment which is affected by the proximity and structure of ear 5A and other physical objects and human head structures that may be in proximity to earbud EB1. Similarly, audio integrated circuit 20B estimates acoustic path $P_2(z)$ combined with removing effects of an electro-acoustic path $S_2(z)$ that represents the response of the audio output circuits of audio integrated circuit 20B and the acoustic/electric transfer function of speaker SPKR2.

Figure 2:
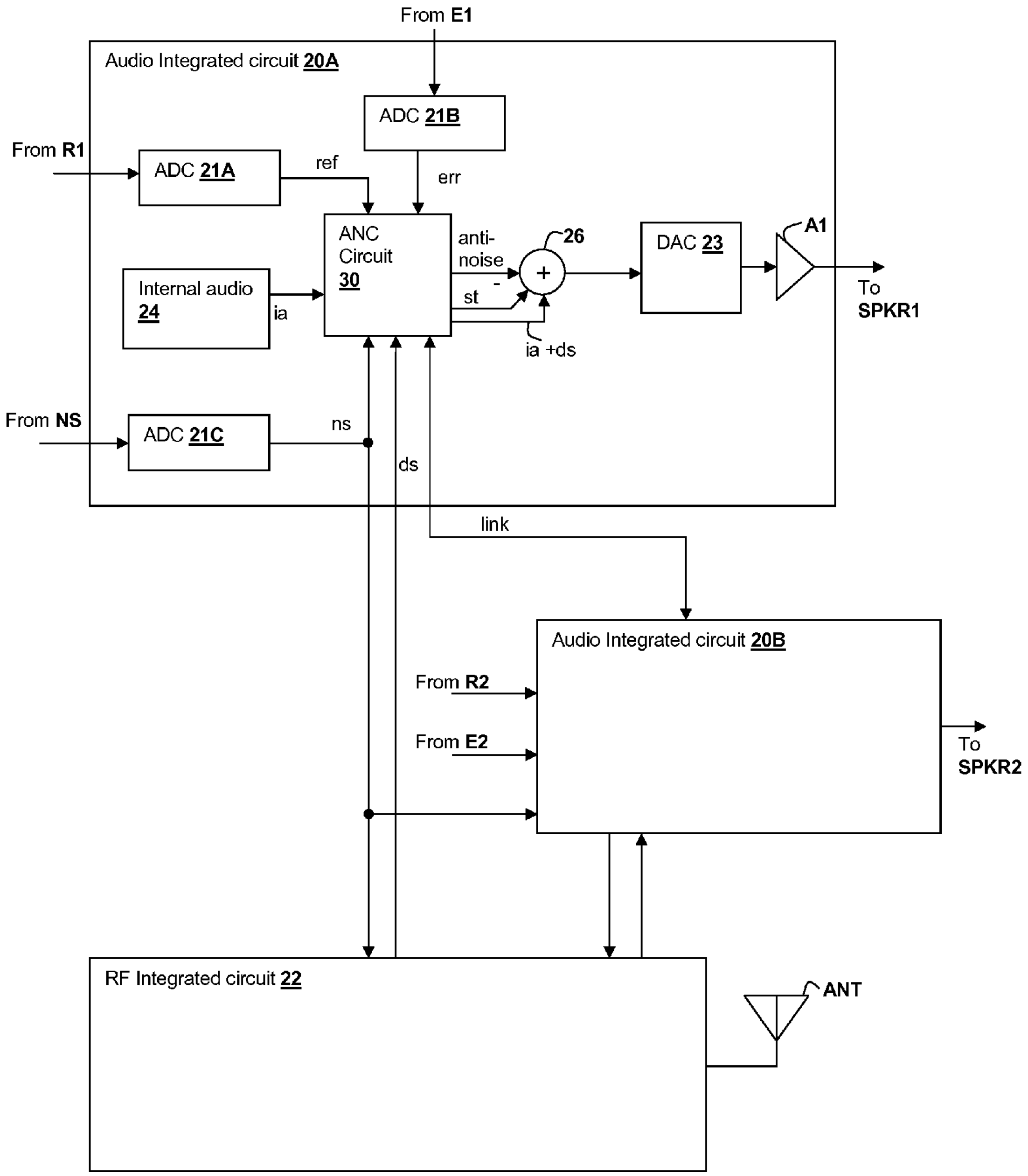
FIG. 2 is a block diagram of circuits within wireless telephone 10 and/or earbuds EB1 and EB2 of FIG. 1A.

Referring now to FIG. 2, circuits within earbuds EB1, EB2 and wireless telephone 10 are shown in a block diagram. The circuit shown in FIG. 2 further applies to the other configurations mentioned above, except that signaling between CODEC integrated circuit 20 and other units within wireless telephone 10 are provided by cables or wireless connections when audio integrated circuits 20A, 20B are located outside of wireless telephone 10, e.g., within corresponding earbuds EB1, EB2. In such a configuration, signaling between a single integrated circuit 20 that implements integrated circuits 20A-20B and error microphones E1, E2, reference microphones R1, R2 and speakers SPKR1, SPKR2 are provided by wired or wireless connections when audio integrated circuit 20 is located within wireless telephone 10. In the illustrated example, audio integrated circuits 20A, 20B are shown as separate and substantially identical circuits, so only audio integrated circuit 20A will be described in detail below.

Audio integrated circuit 20A includes an analog-to-digital converter (ADC) 21A for receiving the reference microphone signal from reference microphone R1 and generating a digital representation ref of the reference microphone signal. Audio integrated circuit 20A also includes an ADC 21B for receiving the error microphone signal from error microphone E1 and generating a digital representation err of the error microphone signal, and an ADC 21C for receiving the near speech microphone signal from near speech microphone NS and generating a digital representation of near speech microphone signal ns. (Audio integrated circuit 20B receives the digital representation of near speech microphone signal ns from audio integrated circuit 20A via the wireless or wired connections as described above.) Audio integrated circuit 20A generates an output for driving speaker SPKR1 from an amplifier A1, which amplifies the output of a digital-to-analog converter (DAC) 23 that receives the output of a combiner 26. Combiner 26 combines audio signals is from internal audio sources 24, and the anti-noise signal anti-noise generated by ANC circuit 30, which by convention has the same polarity as the noise in reference microphone signal ref and is therefore subtracted by combiner 26. Combiner 26 also combines an attenuated portion of near speech signal ns, i.e., sidetone information st, so that the user of wireless telephone 10 hears their own voice in proper relation to downlink speech ds, which is received from radio frequency (RF) integrated circuit 22. Near speech signal ns is also provided to RF integrated circuit 22 and is transmitted as uplink speech to the service provider via antenna ANT.

Figure 3:
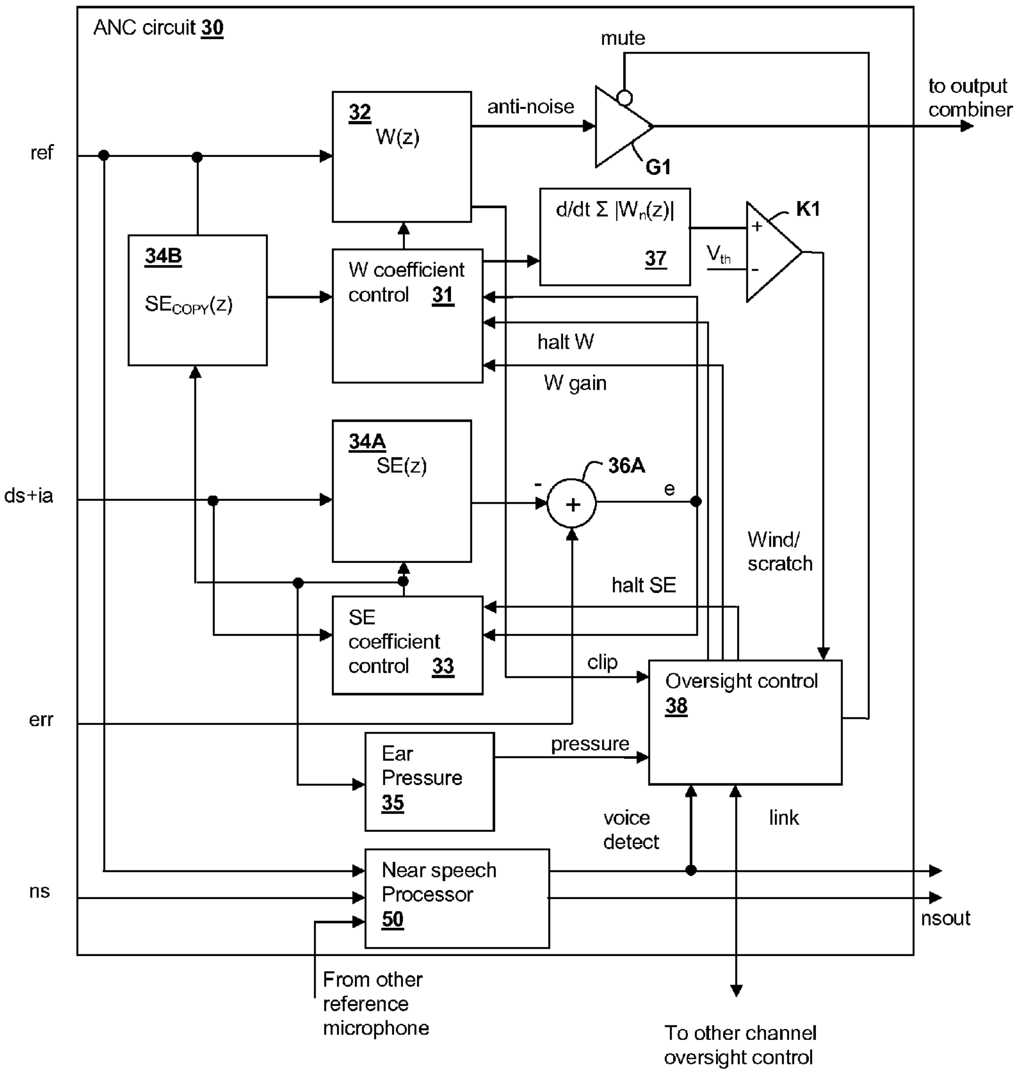
FIG. 3 is a block diagram depicting signal processing circuits and functional blocks within ANC circuit 30 of audio integrated circuits 20A, 20B of FIG. 2.

Referring now to FIG. 3, details of an exemplary ANC circuit 30 within audio integrated circuits 20A and 20B of FIG. 2, are shown. An adaptive filter 32 receives reference microphone signal ref and under ideal circumstances, adapts its transfer function W(z) to be P(z)/S(z) to generate the anti-noise signal anti-noise, which is provided to an output combiner that combines the anti-noise signal with the audio to be reproduced by speaker SPKR, as exemplified by combiner 26 of FIG. 2. A gain block G1 is responsive to a control signal mute to mute the anti-noise signal under certain conditions as described in further detail below. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err. The signals processed by W coefficient control block 31 are the reference microphone signal ref shaped by a copy of an estimate of the response of path S(z) (i.e., response $SE_{COPY}(z)$) provided by filter 34B and another signal that includes error microphone signal err. By transforming reference microphone signal ref with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z).

In addition to error microphone signal err, the other signal processed along with the output of filter 34B by W coefficient control block 31 includes an inverted amount of the source audio (ds+ia) including downlink audio signal ds and internal audio is processed by a filter 34A having response SE(z), of which response $SE_{COPY}(z)$ is a copy. By injecting an inverted amount of source audio (ds+ia) that has been filtered by response SE(z), adaptive filter 32 is prevented from adapting to the relatively large amount of source audio present in error microphone signal err. By transforming the inverted copy of source audio (ds+ia) with the estimate of the response of path S(z), the source audio that is removed from error microphone signal err before processing should match the expected version of source audio (ds+ia) reproduced at error microphone signal err. The source audio amounts match because the electrical and acoustical path of S(z) is the path taken by source audio (ds+ia) to arrive at error microphone E. Filter 34B is not an adaptive filter, per se, but has an adjustable response that is tuned to match the response of adaptive filter 34A, so that the response of filter 34B tracks the adapting of adaptive filter 34A. To implement the above, adaptive filter 34A has coefficients controlled by an SE coefficient control block 33. Adaptive filter 34A processes the source audio (ds+ia) to provide a signal representing the expected source audio delivered to error microphone E. Adaptive filter 34A is thereby adapted to generate a signal from source audio (ds+ia), that when subtracted from error microphone signal err, forms an error signal e containing the content of error microphone signal err that is not due to source audio (ds+ia). A combiner 36A removes the filtered source audio (ds+ia) from error microphone signal err to generate the above-described error signal e.

Within ANC circuit 30, an oversight control logic 38 performs various actions in response to various conditions detected in one or both ANC channels that generally cause action on both ANC channels, as will be disclosed in further detail below. Oversight control logic 38 generates several control signals including control signal halt W, which halts adaptation of W coefficient control block 31, control signal halt SE, which halts adaptation of SE coefficient control block 33, control signal W gain, which can be used to reduce or reset the gain of response W(z), and control signal mute, which controls gain block G1 to gradually mute the anti-noise signal. Table 1 below depicts a list of ambient audio events or conditions that may occur in the environment of wireless telephone 10 of FIG. 1, the issues that arise with the ANC operation, and the responses taken by the ANC processing circuits when the particular ambient events or conditions are detected.

TABLE I

| Type of Ambient Audio Condition or Event detected at earbud EB1 | Cause | Issue | Response |
|---|---|---|---|
| Mechanical Noise at Microphone or instability of the coefficients of W(z) in general | Wind, Scratching, etc. | Unstable anti-noise, ineffective cancelation | Mute anti-noise<br>Stop adapt W(z) in earbud EB1<br>Reset W(z)<br>Optional:<br>Reduce gain of W(z) in earbud EB2 |
| Ear pressure below threshold at earbud EB1 | EB1 removed from ear | User may be trying to hear ambient | Halt adaptation of W(z) in both earbuds EB1, EB2<br>Alternative: reduce gain of W(z) in both earbuds EB1, EB2 |
| Reference microphone signal > Max | Ambient too loud | Anti-noise unable to produce enough output to cancel | Stop Adapting W(z), SE(z) in both channels, optionally mute anti-noise |

TABLE I-continued

| Type of Ambient Audio Condition or Event detected at earbud EB1 | Cause | Issue | Response |
|---|---|---|---|
| Internal Clipping | Ambient too loud | Distortion/clicking | Stop adapt W(z) Optionally mute anti-noise Optional: stop adapting SE(s) reset/backtrack SE(z), hold condition longer on channel opposite detection channel to ensure entire clipping event has ended |

As illustrated in FIG. 3, W coefficient control block 31 provides the coefficient information to a computation block 37 that computes the time derivative of the sum $\Sigma|W_n(z)|$ of the magnitudes of the coefficients $W_n(z)$ that shape the response of adaptive filter 32, which is an indication of the variation overall gain of the response of adaptive filter 32. Large variations in sum $\Sigma|W_n(z)|$ indicate that mechanical noise, such as that produced by wind incident on the corresponding one of reference microphones R1, R2, or varying mechanical contact (e.g., scratching) on the housing of the corresponding earbud EB1, EB2, or other conditions such as an adaptation step size that is too large and causes unstable operation has been used in the system. A comparator K1 compares the time derivative of sum $\Sigma|W_n(z)|$ to a threshold to provide an indication Wind/Scratch to oversight control 38 of a mechanical noise condition. A degree of coupling between the listener's ear and the corresponding one of earbuds EB1, EB2 can be estimated by an ear pressure estimation block 35. Ear pressure estimation block 35 generates an indication, control signal Pressure, of the degree of coupling between the listener's ear and the corresponding one of earbuds EB1, EB2. Oversight control 38 can then use control signal Pressure to determine when to halt adaptation of W(z) for both channels, and reduce the gain of W(z) in the opposite one of earbuds EB1, EB2. Techniques for determining the degree of coupling between the listener's ear and wireless telephone 10 that may be used to implement ear pressure estimation block 35 are disclosed in U.S. Patent Application Publication No. US20120207317A1 entitled "EAR-COUPLING DETECTION AND ADJUSTMENT OF ADAPTIVE RESPONSE IN NOISE-CANCELING IN PERSONAL AUDIO DEVICES", the disclosure of which is incorporated herein by reference. Adaptive filter 32 also provides an indication clip that indicates when the digital values produced by adaptive filter 32 have clipped, or when clipping is expected to occur in the subsequent analog or digital signals representing the anti-noise. In response to assertion of indication clip, oversight control takes actions such as those indicated in Table I and in accordance with one exemplary implementation, takes action for a longer period of time on the channel opposite the channel in which indication clip was asserted, in order to ensure that the ambient conditions causing the clipping have ended. A link signal is provided between the ANC circuit 30 for each of the channels corresponding to earbuds EB1, EB2, so that when oversight control 38 detects a condition that requires action on the adaptation of adaptive filter 32 and other actions such as muting the anti-noise signal, the proper action, which may be a different action as noted above, can also be taken on the opposite channel.

Figure 4:
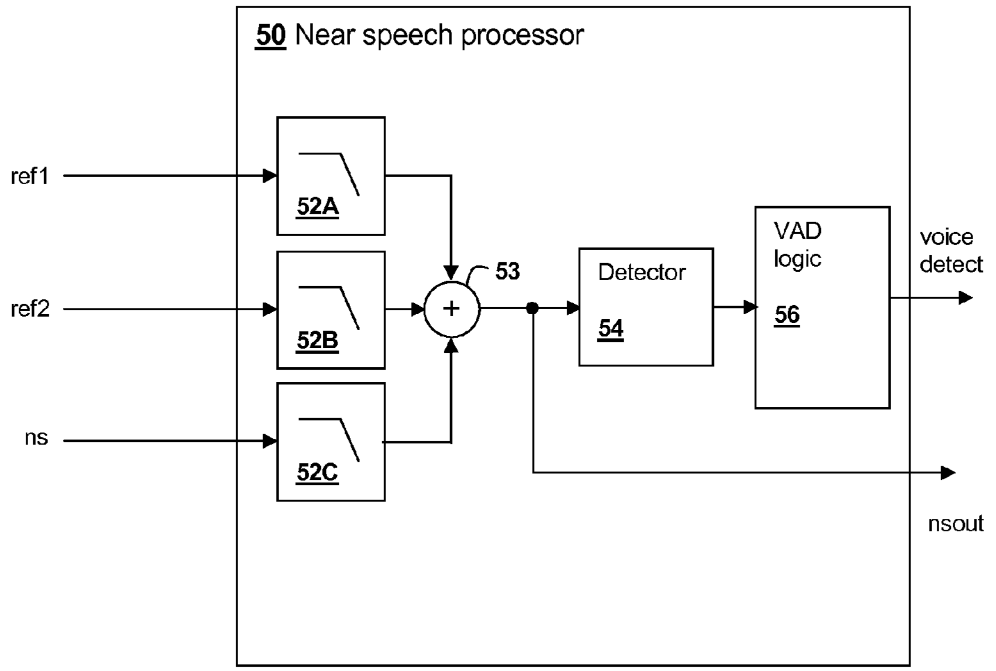
FIG. 4 is a block diagram depicting an exemplary implementation of near-speech processor 50 of FIG. 3.

Referring to FIG. 4, details of a near speech processor 50 that may be included within ANC circuits 30 of FIG. 3 is shown. Near speech processor 50, as illustrated, is only a simplified example of the types of processing that may be performed when two reference microphone signals ref1 and ref2 are available from corresponding earbuds EB1, EB2 and speech is received at a third near speech microphone NS that provides a near speech microphone signal ns. In the illustrated example, each of reference microphone signals ref1, ref2 and near speech microphone signal ns are provided to respective low-pass filters 52A-52C, which remove high frequency content for which the phase between reference microphone signals ref1, ref2 and near speech microphone signal ns would be uncertain due to the physical distances between the corresponding microphones. The filtered reference microphone signals and near speech microphone signal are summed by a combiner 53, which makes a beamformer, since reference microphones R1, R2 of FIG. 1 will generally be equidistant from near speech source (listener's mouth), summing reference microphone signals ref1, ref2 will tend to cancel sounds coming from directions other than directly between reference microphones R1, R2. The phase response of filter 52C may need to be adjusted with respect to filters 52A and 52B in order to match the phase of the beam formed by reference microphone signals ref1, ref2 and the phase of near speech microphone signal ns. The output of combiner 53 can be used as an enhanced near speech output signal nsout having increased amplitude with respect to ambient noise. Another feature of near speech processor 50 uses the enhanced near speech signal nsout to improve voice activity detection (VAD). A level of near speech output signal ns is detected by a detector 54 which provides an input to a VAD logic block 56 in order to distinguish when voice activity is present at sufficient energy over the ambient sounds.

Figure 5:
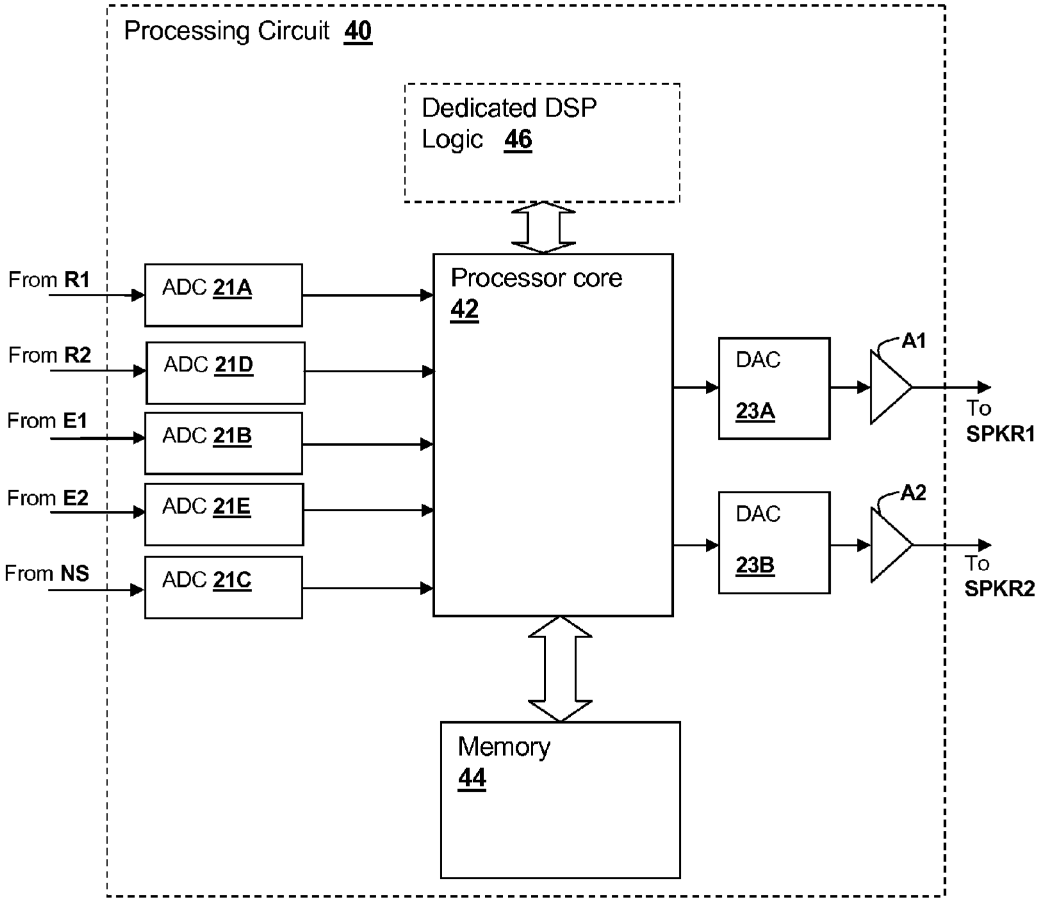
FIG. 5 is a block diagram depicting signal processing circuits and functional blocks within an integrated circuit implementing an ANC system as disclosed herein.

Referring now to FIG. 5, a block diagram of an ANC system is shown for implementing ANC techniques as depicted in FIG. 3 and having a processing circuit 40 as may be implemented within audio integrated circuits 20A, 20B of FIG. 2, which is illustrated as combined within one circuit, but could be implemented as two or more processing circuits that inter-communicate. Processing circuit 40 includes a processor core 42 coupled to a memory 44 in which are stored program instructions comprising a computer program product that may implement some or all of the above-described ANC techniques, as well as other signal processing. Optionally, a dedicated digital signal processing (DSP) logic 46 may be provided to implement a portion of, or alternatively all of, the ANC signal processing provided by processing circuit 40. Processing circuit 40 also includes ADCs 21A-21E, for receiving inputs from reference microphone R1, error microphone E1 near speech microphone NS, reference microphone R2, and error microphone E2, respectively. In alternative embodiments in which one or more of reference microphone R1, error microphone E1 near speech microphone NS, reference microphone R2, and error microphone E2 have digital outputs or are communicated as digital signals from remote ADCs, the corresponding ones of ADCs 21A-21E are omitted and the digital microphone signal(s) are interfaced directly to processing circuit 40. DAC 23A and amplifier A1 are also provided by processing circuit 40 for providing the speaker output signal to speaker SPKR1, including anti-noise as described above. Similarly, DAC 23B and amplifier A2 provide another speaker output signal to speaker SPKR2. The speaker output signals may be digital output signals for provision to modules that reproduce the digital output signals acoustically.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio system, comprising:

a first earspeaker for reproducing a first audio signal including both first source audio for playback to a listener and a first anti-noise signal for countering the effects of ambient audio sounds in an acoustic output of the first earspeaker;

a second earspeaker for reproducing a second audio signal including both second source audio for playback to a listener and a second anti-noise signal for countering the effects of ambient audio sounds in an acoustic output of the second earspeaker;

at least one microphone for providing at least one microphone signal indicative of the ambient audio sounds; and a processing circuit that generates the first anti-noise signal from the at least one microphone signal using a first adaptive filter to reduce the presence of the ambient audio sounds at the first earspeaker in conformity with the at least one microphone signal, wherein the processing circuit generates the second anti-noise signal from the at least one microphone signal using a second adaptive filter to reduce the presence of the ambient audio sounds at the second earspeaker in conformity with the at least one microphone signal, wherein the processing circuit determines a first degree of coupling between the first earspeaker and an ear of the listener and determines a second degree of coupling between the second earspeaker and another ear of the listener, and wherein the processing circuit halts an update of coefficients of both the first adaptive filter and the second adaptive filter in response to detecting that the first degree of coupling indicates that the first earspeaker is loosely coupled to the ear of the listener or that the second degree of coupling indicates that the second earspeaker is loosely coupled to the other ear of the listener, while continuing to generate the first anti-noise signal and the second anti-noise signal.

2. The personal audio system of claim 1, wherein the at least one microphone comprises a first microphone mounted on a housing of the first earspeaker and a second microphone mounted on a housing of the second earspeaker, wherein the processing circuit generates the first anti-noise signal from the first microphone, and wherein the processing circuit generates the second anti-noise signal from the second microphone.

3. The personal audio system of claim 1, wherein the processing circuit further reduces a gain of a response of the second adaptive filter in response to detecting that the first degree of coupling indicates that the first earspeaker is loosely coupled to the ear of the listener.

4. The personal audio system of claim 1, wherein the processing circuit detects clipping in a first audio path including the first adaptive filter and in a second audio path including the second adaptive filter, and wherein the processing circuit takes action on adaptation of both of the first adaptive filter and the second adaptive filter in response to detecting clipping in either of the first audio path or the second audio path.

5. The personal audio system of claim 4, wherein the processing circuit takes action on the second adaptive filter for a longer period of time than taking action on the first adaptive filter in response to detecting clipping in the first audio path.

6. The personal audio system of claim 1, wherein the processing circuit detects that the ambient audio sounds arriving at the first microphone have exceeded a predetermined amplitude threshold, and in response to detecting that ambient audio sounds have exceeded the predetermined amplitude threshold, the processing circuit halts adaptation of both the first adaptive filter and the second adaptive filter.

7. The personal audio system of claim 1, wherein the processing circuit detects scratching on a first housing of the first earspeaker or wind noise at the first earspeaker and does not detect scratching on a second housing of the second earspeaker or wind noise at the second earspeaker, and in response to detecting scratching on the first housing of the first earspeaker or wind noise at the first earspeaker, mutes the first anti-noise signal and halts adaptation of the first adaptive filter and does not mute the second anti-noise signal.

8. The personal audio system of claim 7, wherein the processing circuit, in response to detecting scratching on the first housing of the first earspeaker or wind noise at the first earspeaker, reduces a gain of the second adaptive filter.

9. A method of countering effects of ambient audio sounds by a personal audio system, the method comprising:

first generating a first anti-noise signal from at least one microphone signal using a first adaptive filter to reduce the presence of the ambient audio sounds at a first earspeaker in conformity with the at least one microphone signal;

second generating a second anti-noise signal from the at least one microphone signal using a second adaptive filter to reduce the presence of the ambient audio sounds at a second earspeaker in conformity with the at least one microphone signal;

determining a first degree of coupling between the first earspeaker and an ear of the listener;

determining a second degree of coupling between the second earspeaker and another ear of the listener; and responsive to detecting that the first degree of coupling indicates that the first earspeaker is loosely coupled to the ear of the listener or that the second degree of coupling indicates that the second earspeaker is loosely coupled to the other ear of the listener, halting update of coefficients of both the first adaptive filter and the second adaptive filter, while continuing the first generating and the second generating.

10. The method of claim 9, wherein the at least one microphone comprises a first microphone mounted on a housing of the first earspeaker and a second microphone mounted on a housing of the second earspeaker, wherein the first generating generates the first anti-noise signal from the first microphone, and wherein the second generating generates the second anti-noise signal from the second microphone.

11. The method of claim 10, further comprising reducing a gain of a response of the second adaptive filter in response to detecting that the first degree of coupling indicates that the first earspeaker is loosely coupled to the ear of the listener.

12. The method of claim 9, further comprising detecting clipping in a first audio path including the first adaptive filter and in a second audio path including the second adaptive filter, and further comprising taking action on adaptation of both of the first adaptive filter and the second adaptive filter in response to detecting clipping in either of the first audio path or the second audio path.

13. The method of claim 12, wherein the halting of updates halts updates of coefficients of the second adaptive filter for a longer period of time than the halting of updates of coefficients of the first adaptive filter in response to detecting clipping in the first audio path.

14. The method of claim 9, wherein the detecting detects that the ambient audio sounds arriving at the first microphone have exceeded a predetermined amplitude threshold, and further comprising, in response to detecting that ambient audio sounds have exceeded the predetermined amplitude threshold, halting adaptation of both the first adaptive filter and the second adaptive filter.

15. The method of claim 9, further comprising detecting scratching on a first housing of the first earspeaker or wind noise at the first earspeaker and does not detect scratching on a second housing of the second earspeaker or wind noise at the second earspeaker, and further comprising in response to detecting scratching on the first housing of the first earspeaker or wind noise at the first earspeaker, muting the first anti-noise signal and halting adaptation of the first adaptive filter while not muting the second anti-noise signal.

16. The method of claim 15, further comprising reducing a gain of the second adaptive filter in response to detecting scratching on the first housing of the first earspeaker or wind noise at the first earspeaker.

17. An integrated circuit for implementing at least a portion of a personal audio system, comprising:

a first output for providing a first output signal to a first earspeaker including both first source audio for playback to a listener and a first anti-noise signal for countering the effects of ambient audio sounds in a first acoustic output of the first earspeaker;

a second output for providing a second output signal to a second earspeaker including both second source audio for playback to a listener and a second anti-noise signal for countering the effects of the ambient audio sounds in a second acoustic output of the second earspeaker;

at least one microphone input for receiving at least one microphone signal indicative of the ambient audio sounds; and a processing circuit that generates the first anti-noise signal from the at least one microphone signal using a first adaptive filter to reduce the presence of the ambient audio sounds at the first earspeaker in conformity with the at least one microphone signal, wherein the processing circuit generates the second anti-noise signal from the at least one microphone signal using a second adaptive filter to reduce the presence of the ambient audio sounds at the second earspeaker in conformity with the at least one microphone signal, wherein the processing circuit determines a first degree of coupling between the first earspeaker and an ear of the listener and determines a second degree of coupling between the second earspeaker and another ear of the listener, and wherein the processing circuit halts an update of coefficients of both the first adaptive filter and the second adaptive filter in response to detecting that the first degree of coupling indicates that the first earspeaker is loosely coupled to the ear of the listener or that the second degree of coupling indicates that the second earspeaker is loosely coupled to the other ear of the listener, while continuing to generate the first anti-noise signal and the second anti-noise signal.

18. The integrated circuit of claim 17, wherein the at least one microphone signal comprises a first microphone signal provided from a first microphone mounted on a housing of a first earspeaker and a second microphone signal provided from a second microphone mounted on a housing of a second earspeaker, wherein the processing circuit generates the first anti-noise signal from the first microphone signal, and wherein the processing circuit generates the second anti-noise signal from the second microphone signal.

19. The integrated circuit of claim 17, wherein the processing circuit further reduces a gain of a response of the second adaptive filter in response to detecting that the first degree of coupling indicates that the first earspeaker is loosely coupled to the ear of the listener.

20. The integrated circuit of claim 17, wherein the processing circuit detects clipping in a first audio path including the first adaptive filter and in a second audio path including the second adaptive filter, and wherein the processing circuit takes action on adaptation of both of the first adaptive filter and the second adaptive filter in response to detecting clipping in either of the first audio path or the second audio path.

21. The integrated circuit of claim 20, wherein the processing circuit takes action on the second adaptive filter for a longer period of time than taking action on the first adaptive filter in response to detecting clipping in the first audio path.

22. The integrated circuit of claim 17, wherein the processing circuit detects that the ambient audio sounds arriving at the first microphone have exceeded a predetermined amplitude threshold, and in response to detecting that ambient audio sounds have exceeded the predetermined amplitude threshold, the processing circuit halts adaptation of both the first adaptive filter and the second adaptive filter.

23. The integrated circuit of claim 17, wherein the at least one microphone signal comprises a first microphone signal provided from a first microphone mounted on a housing of a first earspeaker and a second microphone signal provided from a second microphone mounted on a housing of a second earspeaker, wherein the processing circuit detects scratching or wind noise in the first microphone signal and does not detect scratching or wind noise in the second microphone signal, and in response to detecting scratching or wind noise in the first microphone signal, mutes the first anti-noise signal and halts adaptation of the first adaptive filter and does not mute the second anti-noise signal.

24. The integrated circuit of claim 23, wherein the processing circuit, in response to detecting scratching or wind noise in the first microphone signal, reduces a gain of the second adaptive filter.

* * * * *